United States Patent [19]

Villalta et al.

[11] Patent Number: 5,667,481

[45] Date of Patent: Sep. 16, 1997

[54] FOUR BLADE MEDICAL RETRACTOR

[76] Inventors: Josue J. Villalta, 11923 Discovery Cir., Indianapolis, Ind. 46236; Jean Robert Passemard, 8 Rue Dela Tour Aux Saints, Crecy la Chapelle, 77580, France; Jimmie E. Warthan, 3743 Whenner Dr., Indianapolis, Ind. 46226; Jeffrey L. Beaver, 2094 Olivewood Dr., Indianapolis, Ind. 46219

[21] Appl. No.: 382,278

[22] Filed: Feb. 1, 1995

[51] Int. Cl.$^6$ ........................................................ A61B 1/32
[52] U.S. Cl. ........................... 600/224; 600/219; 600/227; 600/231
[58] Field of Search ........................ 600/219, 224, 600/227-28, 231-34, 239; 269/210, 212

[56] References Cited

U.S. PATENT DOCUMENTS

| | | |
|---|---|---|
| 3,038,468 | 6/1962 | Raeuchle . |
| 3,724,449 | 4/1973 | Gauthier .............................. 600/224 |
| 3,750,652 | 8/1973 | Sherwin . |
| 4,130,113 | 12/1978 | Graham . |
| 5,081,983 | 1/1992 | Villalta et al. . |
| 5,183,032 | 2/1993 | Villalta et al. . |
| 5,299,563 | 4/1994 | Seton . |

FOREIGN PATENT DOCUMENTS

| | | |
|---|---|---|
| 542744 | 8/1922 | France . |
| 1700 | 6/1891 | Germany . |
| 445162 | 2/1949 | Italy . |
| 464302 | 6/1951 | Italy . |
| 330629 | 6/1930 | United Kingdom . |

*Primary Examiner*—Richard J. Apley
*Assistant Examiner*—Beverly M. Flanagan
*Attorney, Agent, or Firm*—Woodard, Emhardt, Naughton, Moriarty & McNett

[57] ABSTRACT

A four blade medical retractor for holding open a body or surgical cavity. A first blade is fixedly mounted to the first leg of an L-shaped frame. A second blade is slidably mounted to the second leg of the frame and includes a spring biased pawl to control motion of the second blade relative to the first blade. A third blade is slidably mounted to the first leg and also includes a pawl to control motion of the third blade along the first leg. A carrier mounted to the second leg holds a fourth blade which is movable both along the length of the second leg and also to and from the third blade.

16 Claims, 4 Drawing Sheets

FOUR BLADE MEDICAL RETRACTOR

BACKGROUND OF THE INVENTION

1. Field of the Invention

This invention relates to devices for holding open a surgical cavity.

2. Description of the Prior Art

In U.S. Pat. Nos. 5,081,983 and 5,183,032 and the allowed U.S. patent application Ser. No. 08/149,066, all owned by the assignee hereof: we have described different medical retractors for use in holding open body cavities including surgical cavities in humans or animals. A variety of retractors have been provided in addition to the retractors described in the aforementioned retractors. For example, various retractors are disclosed in the following U.S. Pat No. 3,750,652 issued to Sherwin; U.S. Pat. No. 4,130,113 issued to Graham; and U.S. Pat. No. 4,667,657 issued to Kulik et at. The Sherwin retractor includes a pair of blades used to separate a patient's knee with the blades being forcefully driven apart by means of a worm gear. The Graham Patent discloses a plurality of flesh engaging blades arranged on a circular frame through which the surgeon operates. Finally, the Kulik et al. Patent discloses a plurality of blades movable apart by means of a rod slidably mounted to the retractor frame. Foreign patents include Italian Patents 445162 and 464302; British Patent 330629; French Patent 542744; and German Patent 1700. The two Italian patents disclose a plurality of blades inserted into the cavity along with a stationary plate. Wing nuts or other members protrude outwardly from the retractor allowing the surgeon to possibly snag the surgical gloves thereon. The British patent discloses a plurality of blades mounted to a ring structure through which the surgeon examines the patient. The French patent also discloses a plurality of blades mounted to a ring shape frame. Finally, the German patent discloses an expandable retractor which utilizes a worm gear projecting to the side of the retractor frame.

In order to facilitate the use of a retractor, it is desirable that one person be able to easily manipulate the various blades of the retractor for insertion into the surgical cavity. It is therefore desirable that the blades be mounted on a relatively simple frame. The U.S. Pat. No. 3,038,468 issued to Raeuchle, U.S. Pat. No. 3,724,449 issued to Gauthier and U.S. Pat. No. 5,299,563 issued to Seten all disclose frames having a plurality of retractor blades mounted thereto.

Despite the medical retractors provided to date, there is still need for a retractor which may be used by a surgeon without assistance from another with the surgeon being able to gradually open the wound, incision or body cavity to the desired size. Such a retractor and method of holding open the cavity must ensure that the retractor is stable relative to the patient and does not become accidentally dislodged.

A major disadvantage of the prior retractors is that the structures typically provide for a variety of fasteners and other elements which protrude outwardly above the retractor snagging the surgeons glove and surgical thread. Thus, there is a need for a retractor having a smooth flat upwardly facing surface with the retractor resting atop the patient in a stable manner while the blades protrude downwardly into the cavity. Disclosed herein is such a retractor.

SUMMARY OF THE INVENTION

One embodiment of the present invention is a medical retractor for holding open a surgical cavity comprising a frame, a first blade mounted to the frame and projecting downwardly therefrom, a second blade initially positioned adjacent the first blade and slidably mounted to the frame and movable apart from the first blade along a first axis to spread apart opposing sides of the surgical cavity, a third blade pivotally mounted to the frame and pivotally movably from above the surgical cavity and into the surgical cavity once the first blade and the second blade are spread apart and a fourth blade insertable into the surgical cavity and then slidably mountable to the frame movable away from the third blade further opening the surgical cavity along a second axis.

It is an object of the present invention to provide a new and improved medical retractor.

Another object of the present invention is to provide a retractor which maximizes the visual and operating area available within the cavity.

A further object of the present invention is to provide a medical retractor which does not include upwardly protruding elements such as fastening devices.

Yet another object of the present invention is to provide a medical retractor for holding open a body cavity and including a pair of pre-assembled retractor blades and a pair of retractor blades added to the assembly as the cavity is open.

Related objects and advantages of the present invention will be apparent from the following description.

DESCRIPTION OF THE PREFERRED EMBODIMENT

Figure 1:
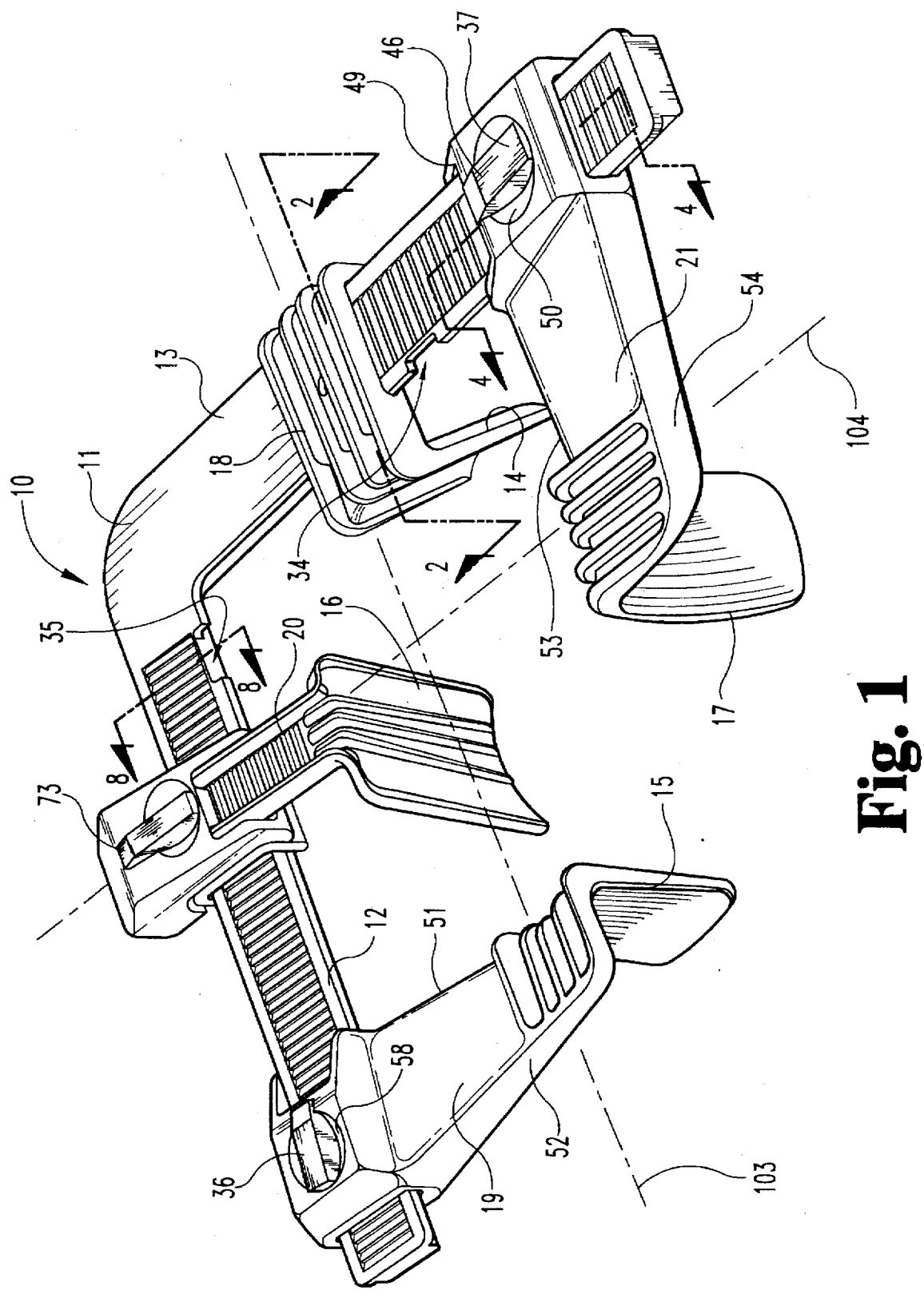
FIG. 1 is a perspective top view of the retractor incorporating the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown the preferred embodiment of the four blade medical retractor 10 incorporating the present invention. Retractor 10 is utilized for holding open a body cavity such as a surgical cavity. The retractor includes a frame 11 with a first leg 12 and a second leg 13 integrally joined together in an L-shaped configuration. Four downwardly extending blades 14, 15, 16, and 17 are mounted respectively by arms 18, 19, 20 and 21 to frame 11. Blades 14 and 17 are mounted to leg 13 of the frame, whereas the remaining blades 15 and 16 are mounted to leg 12 of the frame.

Figure 2:
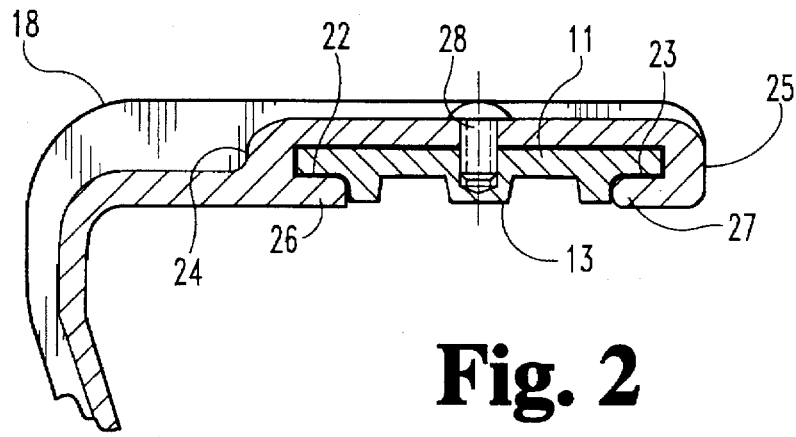
FIG. 2 is a fragmentary enlarged cross-sectional view taken along the line 2—2 of FIG. 1 and viewed of the direction of the arrows.

Frame 11 has a reduced bottom width forming a pair of ledges 22 and 23 (FIG. 2) which extend the length of leg 13 and leg 12. Blade arm 18 is fixedly mounted to leg 13 and includes a pair of downwardly extending sides 24 and 25 with mutually facing and inwardly turned ends 26 and 27 positioned adjacent and below respectively ledges 22 and 23. Arm 18 may initially be installed onto frame 11 by sliding arm 18 onto leg 13 prior to the installation of blade anon 21. A conventional fastening device, such as a bolt 28, fixedly secures arm 18 to the frame. A plurality of internally threaded holes may be provided on leg 13 to allow the mounting of arm 18 at different location along the length of leg 13.

Blade arms 19 and 21 are slidably mounted respectively to frame legs 12 and 13. Blade arm 21 (FIG. 3) includes a proximal end located adjacent frame 11 and includes a channel 31 to slidably receive frame leg 13. The sides 29 and 30 of the proximal end of arm 21 define channel 31 and include respectively inwardly turned ends or ridges 32 and 33 positioned adjacent and immediately below ledges 22 and 23 of leg 13. End 32 of channel side 29 extends only partially along the length of channel 31 whereas end 33 of side 30 extends the entire length of the channel.

In order to install blade arm 21, the arm is positioned vertically and perpendicularly to the horizontally extending frame leg 13 while positioning end 33 immediately adjacent and beneath ledge 23. Blade 17 is then pivoted downwardly in a counterclockwise direction as viewed in FIG. 1 to allow end 32 to pass through recess 34 (FIG. 1) of frame leg 13 until blade arm 21 is in a horizontal position along with frame leg 13. Blade 21 may then be moved away from blade 14 thereby positioning end 32 adjacent and beneath ledge 22 of frame leg 13 securing the blade arm to the frame.

Blade arm 19 is mounted in an identical manner as described for blade arm 21 with frame leg 12 including a recess 35 to receive the inwardly projecting ridge or end of arm 19 identical to end 32. Blade arm 19 includes a channel identical to channel 31 and has an outer end extending the length of the channel identical to ridge 33 which is positioned immediately adjacent and below the outer ledge of leg 12. Likewise, the channel of arm 19 includes an inwardly projecting end identical to end 32 projecting only a portion of the length of the channel. Thus, arm 19 may be initially installed to frame leg 12 in a manner identical to the installation of blade arm 21 in that frame leg 12 includes a recess 35 to receive the shorter channel ridge as arm 19 is pivoted downward.

Figure 3:
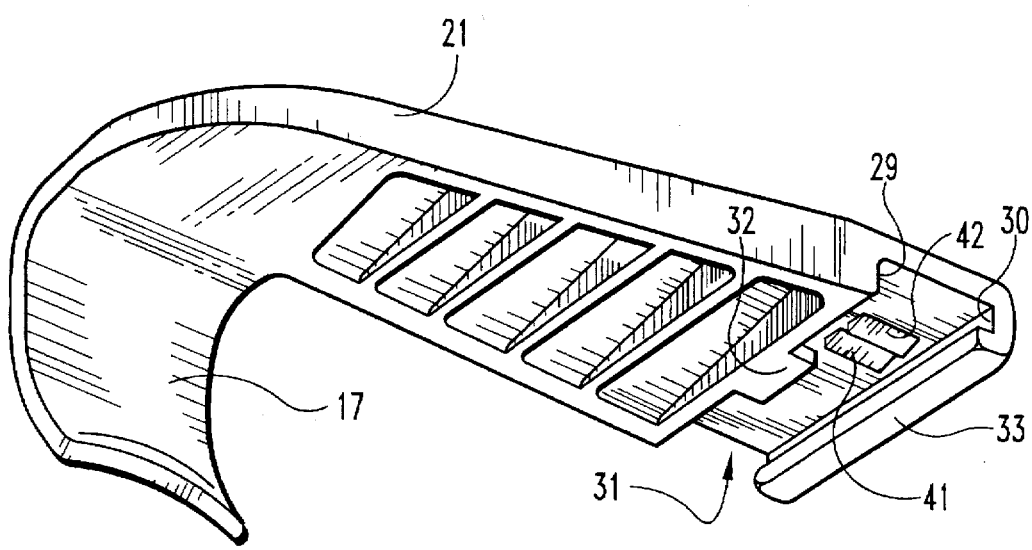
FIG. 3 is a bottom perspective view of a retractor blade.
Figure 4:
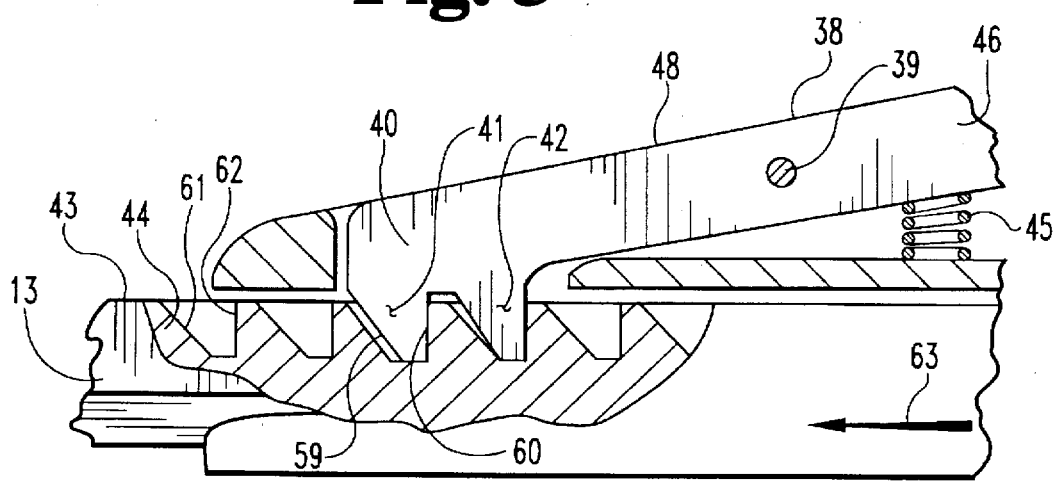
FIG. 4 is a fragmentary enlarged cross-sectional view taken along the line 4—4 of FIG. 1 and viewed in the direction of the arrows.

Blade arms 19 and 21 have releasable locking means for securing in place the arms along the length of each frame leg. Locking means 36 and 37 are identical and thus the following description or locking means 37 will apply equally to locking means 36. Locking means 37 includes a spring biased member 38 pivotally mounted by pin 39 to arm 21 and positioned along the length of the arm located immediately above frame leg 13. One end 40 of member 38 includes a pair of downwardly extending teeth 41 and 42 which are extendable into a channel 31 (FIG. 3). The upwardly facing surface 43 of frame leg 13 includes a plurality of tooth shaped ridges 44 extending across the width of the frame leg. Ridges 44 are shaped to complimentarily receive the downwardly extending teeth 41 and 42. A conventional spring, such as helical spring 45, is positioned between arm 21 and member 38 and located on a side of pin 39 opposite of teeth 41 and 42. Spring 45 is operable to urge member 38 to pivot in a counterclockwise direction as viewed in FIG. 4 to urge teeth 41 and 42 into locking engagement with ridges 44. Likewise, spring 45 is yieldable to allow the user to depress end 46 (FIG. 1) of member 38 thereby pivoting member 38 in an opposite direction and allowing disengagement of teeth 41 and 42 from ridges 44 and allowing the arm 21 to then be moved along the length of frame leg 13 to the desired position whereupon end 46 is released thereby locking the arm and blade in position. Member 38 is shaped so that when engaged with ridges 44, the entire top surface 48 (FIG. 4) of member 38 is flush or recessed relative to the top surface 49 (FIG. 1) of arm 21. A finger shaped depression 50 surrounding end 46 of member 38 allows the user to push downwardly end 46 to disengage the member teeth from the frame ridges.

Blade arms 19 and 21 and blades 15 and 17 are identical, except as noted, having the same channels and locking means for holding the arms in position along frame legs 12 and 13. Frame leg 12 thus includes a plurality of ridges extending across the width of its upwardly facing surface thereof identical to ridges 44. Since frame 11 has an L-shaped configuration, one difference between arms 19 and 21 and blades 15 and 17 is that arm 19 and blade 15 form a right hand configured blade whereas arm 21 and blade 17 form a left hand configured blade. That is, when arm 19 is mounted to leg 12, the teeth of locking means 36 are located to side 52 of the arm as compared to side 51 with blade 15 being located adjacent side 51 to face blade 14. Thus, finger recess 58 is located on arm 19 closer to side 51 than side 52. On the other hand, teeth 41 and 42 of locking means 37 are located closer to side 54 of arm 21 as compared to side 53. Blade 17 is located adjacent side 53 to face blade 16.

The teeth and ridges are configured to allow the blades to move outwardly without depressing locking means 36 and 37 but prevent inward movement of the blades until the locking means are depressed. For example, tooth 41 (FIG. 4) has a slanted surface 59 and a vertical surface 60 positionable adjacent the slanted surface 61 and vertical surface 62 formed by adjacent ridges. Thus, movement of arm 21 toward the outer distal end of leg 13 in the direction of arrow 63 is allowed even though locking means 38 is not depressed at finger recess 50 since slanted surface 59 will simply ratchet over slanted surface 61 to the desired position. Movement of the blade in the direction opposite to arrow 63 is prevented since surfaces 60 and 62 abut and are arranged perpendicular to the direction of motion until end 46 of locking means 38 is depressed. In this manner, the surgeon may move blade 15 and blade 17. away from respectively blades 14 and 16 without depressing locking means 36 and 37.

Figure 5:
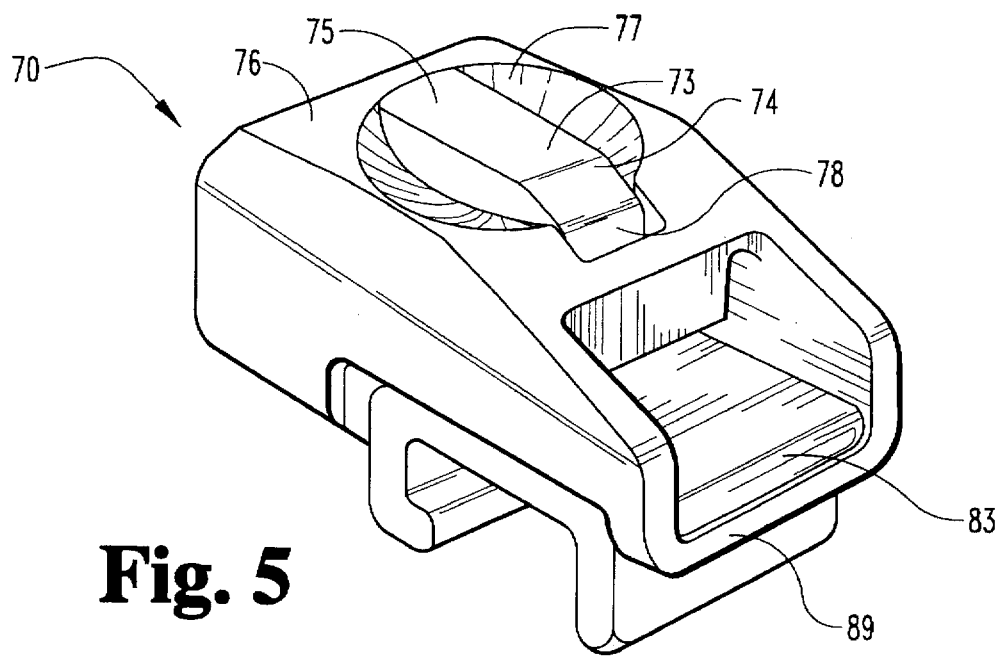
FIG. 5 is a perspective view of a retractor blade holder.
Figure 6:
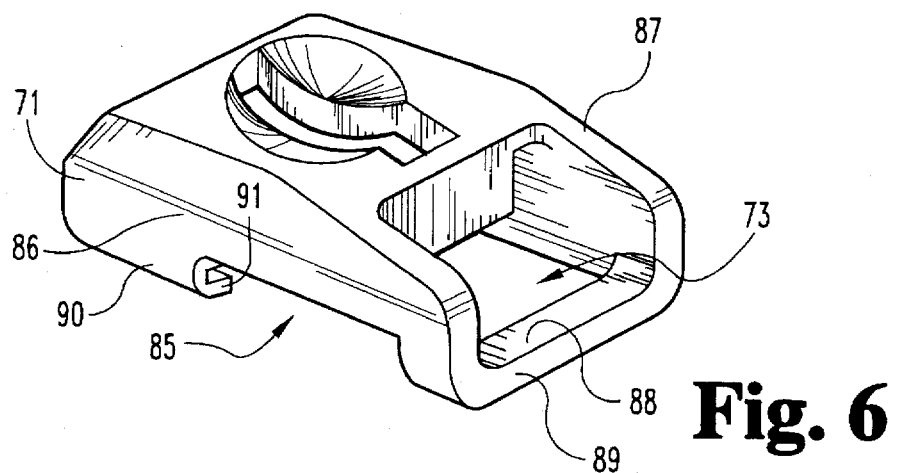
FIG. 6 is a perspective view of the top portion of the holder of FIG. 5.
Figure 7:
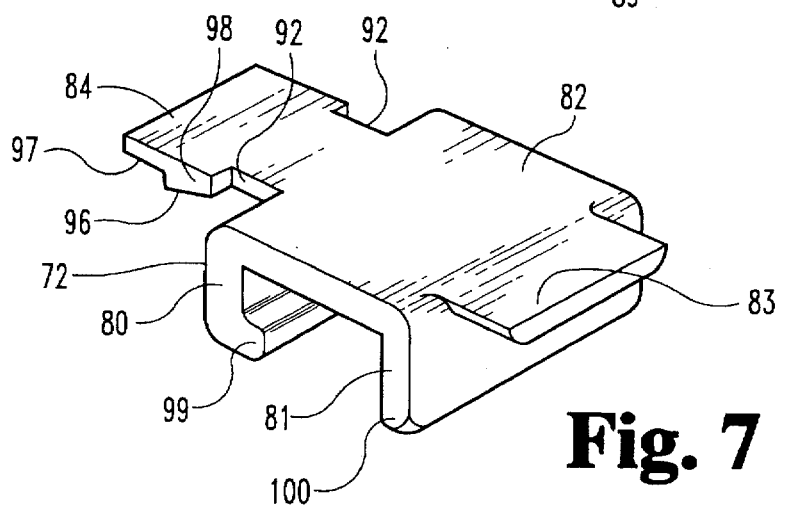
FIG. 7 is a perspective view of the bottom portion of the holder of FIG. 5.

Blade 16 is provided with two degrees of motion in that the blade may move along the length of frame leg 12 and also may be moved to and from blade 17. A carrier 70 (FIG. 5) slidably mounts the blade and arm to the frame providing for the two degrees of motion. Carrier 70 includes a top portion 71 (FIG. 6) and a bottom portion 72 (FIG. 7) mounted together. Top portion 71 includes a channel 73 extending through the length thereof which slidably receives blade arm 20. A locking device 73 identical to devices 36 and 37 is provided to control movement of the blade to and from blade 17. Locking device 73 includes a pivotally mounted member 74 having a top surface 75 flush with the top upwardly facing surface 76 of the carrier. A finger shaped depression 77 surrounds the proximal end 75 of member 74 which is pivotally mounted intermediate its length by a pin secured to carrier 70. The opposite end 78 of member 74 is provided with a pair of downwardly extending teeth identical to teeth 41 and 42 which project into channel 73 and lockingly engage the ridges extending across the width of arm 20. The ridges and teeth are identical to those previously described for locking means 37 and therefore allow the surgeon to move blade 16 in a direction away from blade 17 without depressing proximal end 75 whereas end 75 must be depressed thereby compressing the helical spring located therebeneath and pivoting the teeth of member 74 apart from the ridges extending across arm 20 to allow the surgeon to then move blade 16 toward blade 17.

The bottom portion 72 (FIG. 7) of the carrier has a U-shaped main body with downwardly extending sides 80 and 81 integrally joined to a top wall 82. A forwardly extending lip 83 and a rearwardly extending lip 84 are aligned with and are integrally attached to top wall 82. The side walls 86 and 87 (FIG. 6) of the top portion of the carrier are recessed at location 85 to receive therein the side walls 80 and 81 of the bottom portion of the carrier. Lip 83 extends into channel 73 and immediately over the upwardly facing surface 88 formed by the forward wall 89 of the top half of the carrier. The rearwardly extending lip 84 is also positioned within channel 73. Side walls 86 and 87 each have a lower edge portion 90 with an inwardly turned tab 91 which extends only a portion of the length of the bottom edge 90. Rearward lip 84 is reduced in thickness at locations 92 to allow the inwardly projecting tabs 91 of walls 86 and 87 to pass from a position atop lip 84 through the indented portions at locations 92 and to an eventual position beneath rear lip 84. Bottom portion 72 of the carrier may then be moved in a direction from tab 91 toward forward wall 89 of the top half portion 71 of the carrier positioning tabs 91 beneath the slanted surfaces 96 of a ratchet tooth 98 formed on the bottom surface of rear lip 84 and extending across the width thereof. Continued movement of bottom portion 72 relative to portion 71 will eventually position tabs 91 beneath the horizontal surface 97 and behind ratchet 98 thereby securing the top half and bottom half portions of carrier 70 together.

Figure 8:
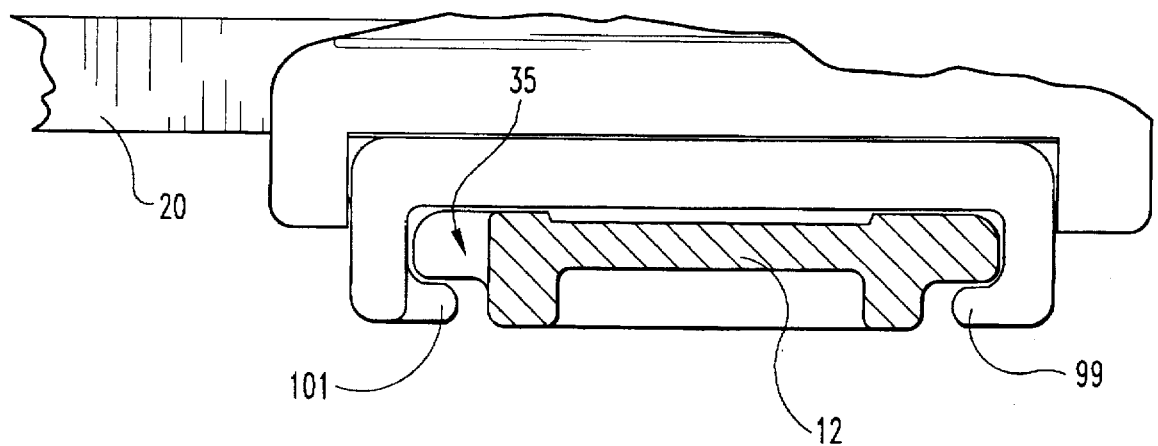
FIG. 8 is a fragmentary enlarged cross-sectional view taken along the line 8—8 of FIG. 1 and viewed in the direction of the arrows.

Carrier 70 is slidably mounted to frame leg 12 but is not locked in place along any particular lengthwise location on the frame leg. Side wall 80 of the carrier has an inwardly extending distal end 99 forming a ridge extending across the entire width of the carrier and positioned adjacent and immediately beneath the outer ledge of frame leg 12 in a manner similar to the positioning of end 33 relative to ledge 23. Likewise, the bottom end 100 of side wall 81 includes a portion thereof which extends inwardly facing end 99 forming an inwardly projecting tab 101 (FIG. 8) which extends only across a portion of the width of the carrier. In a manner similar to the mounting of arm 21, recess 35 (FIG. 1) receives tab 101 as carrier 70 is mounted to the frame leg. The channel formed by side walls 80 and 81 is perpendicularly arranged relative to the channel 83 allowing perpendicular motion of the blade arm 20 relative to frame leg 12.

The mutually facing surfaces of blades 14 and 15 are ribbed configured and are intermeshable to minimize any spacing between the main bodies of blades 14 and 15 when they are initially positioned together for insertion into the surgical cavity. In other words, the ribs of blade 14 are offset relative to the ribs of blade 15 allowing the ribs of blade, 14 to move between the ribs of blade 15. Likewise, the mutually facing surfaces of blades 16 and 17 have mutually facing ribbed and intermeshable surfaces.

Locking means 36 when unlocked allows blade 15 to move to and from blade 14 along axis 103 whereas when the teeth of locking means 36 are locked to the ridges facing upwardly on frame leg 12, blade 15 may be moved only along axis 103 in a direction apart from blade 14 and held positioning blades 14 and 15 at the opposite body cavity extremes.

Likewise, locking means 37 when in an unlocked condition, that is, whereat the teeth are separated from frame leg 13 allow blade 17 to be moved both to and from blade 16 along axis 104. When locking means 37 is in the locked condition, blade 17 may be moved only along axis 104 in a direction away from blade 16.

Locking means 73 when unlocked allows blade 16 to be moved to and from blade 17 independent of blade 17 and also independent of movement of carrier 70 along the length of frame leg 12. The locking means 36, 37 and 73 along with the top surface of frame 11 and the blade arms are smooth and form a snag free upwardly facing surface.

Retractor 10 is initially provided to the surgeon with blades 14 and 15 assembled to frame 11 with blade 15 being positioned immediately adjacent blade 14. Blade 14 and arm 18 may be integrally attached to frame leg 13 or may be fastened to the frame as previously described. The surgeon initially inserts blades 14 and 15 in to the surgical cavity. Next, blade 15 is moved to the left as viewed in FIG. 1 to spread apart the opposing sides of the surgical cavity. Blade 17 and arm 21 are then mounted to frame leg 13 as previously described with blade 17 then pivoting downward in a counterclockwise direction as viewed in FIG. 1 from a position atop the surgical cavity until eventually blade 17 extends into the surgical cavity. Arm 21 is then moved away from recess 34 and blade 14 further opening the surgical cavity. Last, blade 16 along with carrier 70 are mounted to frame leg 12 in a manner similar to the mounting of arm 21 and blade 17. That is, blade 16 is positioned above frame leg 12 with arm 20 extending vertically. Distal end 99 (FIG. 8) of the carrier is in position adjacent the outside ledge of the frame leg with arm 20 along with the blade and carrier then pivoting in a clockwise direction as viewed from the left in FIG. 1 enabling tab 101 to pass through recess 35. Carrier 70 may be positioned at the appropriate location along the length of frame leg 12 automatically centering blade 16 within the surgical cavity. Blade 16 is then moved in a direction away from blade 17 to the opposite cavity extreme.

Many variations are contemplated and included in the present invention. For example, the top portion and bottom portion of carrier 70 may be secured together by means of conventional fastening devices in lieu of tab 91 and ratchet 98.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A medical retractor for holding open a body cavity comprising:

a frame having a first leg and a second leg fixedly joined together in an L-shaped configuration;

a first arm mounted to said first leg;

a first blade joined to said first arm and extending downwardly from said frame;

a second arm slidably mounted to second leg of said frame;

a second blade joined to said second arm and extending downwardly from said frame, said second blade spaced from said first blade a first distance along a straight first axis;

first locking means between said second arm and said second leg of said frame and having an unlocked condition whereat said second blade may be moved both to and from said first blade only along said first axis to allow insertion of said first blade and said second blade into a body cavity and having an unlocked condition whereat said second blade may be moved only along said first axis apart from said first blade and held positioning said first blade and said second blade along said first axis at opposite cavity extremes;

a third arm slidably mounted to said first leg of said frame;

a third blade joined to said third arm and extending downwardly from said frame;

a carrier slidably mounted to said second leg of said frame and movable along said second leg in a lengthwise direction of said second leg;

a fourth blade slidably and pivotably mounted to said carrier and movable in a direction perpendicular to said lengthwise direction and extending downwardly from said frame, said fourth blade spaced from said third blade a second distance along a straight second axis;

second locking means between said third arm and said first leg of said frame and having an unlocked condition whereat said third blade may be moved both to and from said fourth blade only along said second axis to allow insertion of said third blade and said fourth blade into a body cavity and having a locked condition whereat said third blade may be moved only along said second axis away from said fourth blade and held positioning said third blade and said fourth blade along said second axis at opposite cavity extremes; and, third locking means between said carrier and said fourth blade and having, an unlocked condition whereat said fourth blade may be moved along said second axis independent of movement of said third blade along said second axis and independent of movement of said carrier along said lengthwise direction of said second leg to allow insertion of said fourth blade into said cavity whereat said fourth blade may be moved away from said third blade.

2. The retractor of claim 1 wherein:

said first blade and said second blade have mutually facing ribbed intermeshable surfaces minimizing blade spacing therebetween.

3. The retractor of claim 1 wherein:

said frame includes an upwardly facing ratcheted shaped surface and said first locking means includes a spring biased pawl releasably lockable with said upwardly facing surface.

4. The retractor of claim 3 wherein:

said second locking means and said third locking means include spring biased pawls releasably lockable with said upwardly facing surface.

5. The retractor of claim 1 wherein:

said fourth blade includes a fourth arm extending therefrom and said carrier includes a first channel slidably receiving said fourth arm and a second channel arranged perpendicularly to said first channel slidably receiving said second leg, said third locking means operable to releasably lock said fourth arm in said first channel while allowing movement of said second leg in said second channel.

6. A medical retractor for holding open a surgical cavity comprising:

a base having a first leg and a second leg forming an L-shaped configuration, said first leg and said second leg having an upwardly facing toothed surface and a downwardly facing ledge;

a first blade mounted to said first leg;

a second blade slidably mounted to said second leg and movable along a length thereof to and from said first blade along a straight first axis, said second blade including a stop contacting said ledge to hold said second blade on said second leg;

a third blade slidably mounted to said first leg, said third blade including a stop contacting said ledge to hold said third blade on said first leg;

a fourth blade slidably mounted to said second leg and movable to and from said third blade along a straight second axis perpendicularly arranged to said first axis, said fourth blade including a stop contacting said ledge to hold said fourth blade on said second leg;

first means lockingly engageable with said upwardly facing toothed surface to releasably hold said second blade apart from said first blade a first distance; and second means lockingly engageable with said upwardly facing toothed surface to releasably hold said fourth blade apart from said third blade a second distance holding said cavity open when all blades are inserted therein, said first means and said second means located with said base to form a snag free upwardly facing surface.

7. The retractor of claim 6 wherein:

said fourth blade includes an extension and a carrier, said carrier having a first channel slidably engaging said second leg and a second channel slidable engaging said extension allowing said fourth blade to move along a length of said second leg and also to move to and from said third blade.

8. The retractor of claim 7 wherein:

said base includes an indent in said ledge, said carrier includes a projection normally contacting said ledge to hold said fourth blade on said second leg with said carrier movable to position said projection adjacent said indent and press therethrough to facilitate removal and installation of said fourth blade on said second leg.

9. The retractor of claim 8 wherein:

said carrier includes a lower portion with said first channel formed therein and an upper portion with said second channel formed therein, said upper portion has a mouth leading into said second channel receiving said extension, said lower portion includes a first catch which extends into said mouth and a second catch secured to said upper portion, said first catch and said second catch extending from the opposing ends of said lower portion limiting motion between said upper portion and said lower portion.

10. The retractor of claim 8 wherein:

said first means and said second means include spring biased pawls releasably lockable with said upwardly facing toothed surface.

11. A medical retractor for holding open a surgical cavity comprising:

a frame;

a first blade mounted to said frame and projecting downwardly therefrom;

a second blade initially positioned adjacent said first blade and slidably mounted to said frame and movable apart from said first blade along a first axis to spread apart opposing sides of the surgical cavity;

a third blade pivotally mounted to said frame and pivotally movably from atop said surgical cavity and into said surgical cavity once said first blade and said second blade are spread apart, said third blade being slidably mounted to said frame and movable along both said first axis and along a second axis perpendicularly away from said first axis further opening said surgical cavity; and, a fourth blade insertable into said surgical cavity and then slidably mountable to said frame movable away from said third blade further opening said surgical cavity along said second axis.

12. The retractor of claim 11 and further comprising:

locking devices to secure said second blade, said third blade, and said fourth blade in place once inserted into and opening said surgical cavity.

13. The retractor of claim 12 wherein:

said frame includes upwardly projecting teeth and said locking devices include spring biased pawls with downwardly projecting teeth matingly engageable with said upwardly projecting teeth.

14. The retractor of claim 13 wherein:

said third blade is slidably and pivotally mounted on said frame.

15. The retractor of claim 14 wherein:

said frame includes a first leg and a second leg integrally joined together in a L-shaped configuration with said first blade and said fourth blade mounted to said first leg and said second blade and said third blade mounted to said second leg.

16. The retractor of claim 15 wherein:

said third blade includes an extension and a carrier, said carrier has a first channel slidably receiving said second leg and a second channel perpendicularly arranged to said first channel and slidably receiving said extension.

* * * * *